United States Patent [19]

Smith et al.

[11] Patent Number: 5,776,060

[45] Date of Patent: Jul. 7, 1998

[54] METHOD AND APPARATUS FOR MEASURING BLOOD OXYGEN SATURATION WITHIN A RETINAL VESSEL WITH LIGHT HAVING SEVERAL SELECTED WAVELENGTHS

[75] Inventors: Matthew H. Smith; Russell A. Chipman, both of Madison, Ala.; Thomas E. Minnich, North Little Rock, Ark.

[73] Assignee: University of Alabama in Huntsville, Huntsville, Ala.

[21] Appl. No.: 803,065

[22] Filed: Feb. 20, 1997

[51] Int. Cl.$^6$ ....................................................... A61B 5/00
[52] U.S. Cl. ............................ 600/340; 600/318; 128/920
[58] Field of Search .................................... 600/300, 301, 600/318, 320, 322, 323, 340; 128/920, 923, 924

[56] References Cited

U.S. PATENT DOCUMENTS

| | | |
|---|---|---|
| 3,847,483 | 11/1974 | Shaw et al. . |
| 4,114,604 | 9/1978 | Shaw et al. . |
| 4,166,695 | 9/1979 | Hill et al. . |
| 4,253,744 | 3/1981 | Sawa . |
| 4,305,398 | 12/1981 | Sawa . |
| 4,350,163 | 9/1982 | Ford, Jr. et al. . |
| 4,485,820 | 12/1984 | Flower . |

(List continued on next page.)

OTHER PUBLICATIONS

Hickam, John B., Frayser, Regina, Ross, Joseph C., A Study Of Retinal Venous Blood Oxygen Saturation In Human Subjects By Photographic Means, *Circulation*, vol. XXVII, Mar. 1963, pp. 375–384.

Van Assendelft, O.W., Spectrophotometry Of Haemoglobin Derivatives, Thomas, Springfield, IL 1970), pp. 55–59.

Laing, R.A., Danisch, L.A., Young, L.R., The Choroidal Eye Oximeter: An Instrument For Measuring Oxygen Saturation Of Choroidal Blood In Vivo, *IEEE Transactions On Biomedical Engineering*, vol. BME–222, No. 3, May 1975, pp. 183–195.

Cohen, Allen J., Laing, Ronald A., Multiple Scattering Analysis Of Retinal Blood Oximetry, *IEEE Transactions On Biomedical Engineering*, vol. BME–23, No. 5, Sep. 1976, pp. 391–399.

Roberts, D. Aaron, Analysis Of Vessel Absorption Profiles In Retinal Oximetry, *Medical Physics*, vol. 14, No. 1, Jan./Feb. 1987, pp. 124–130.

Delori, Francois C., Noninvasive Technique For Oximetry Of Blood In Retinal Vessels, *Applied Optics*, vol. 27, Mar. 15, 1988, pp. 1113–1125.

*Primary Examiner*—Jennifer Bahr
*Assistant Examiner*—Eric F. Winakur
*Attorney, Agent, or Firm*—Bell Seltzer Intellectual Property Group of Alston & Bird LLP

[57] ABSTRACT

The method and apparatus for measuring the oxygen saturation of blood within a retinal vessel illuminates the retinal vessel with light having a combination of wavelengths selected to reduce the error in the measured blood oxygen saturation. The oxygen saturation measuring method and apparatus illuminates a retinal vessel with light having the selected combination of wavelengths. For example, the oxygen saturation measuring method and apparatus can illuminate the retinal vessel with light having a first wavelength between 460 nm and 503 nm, a second wavelength between 600 nm, and 770 nm and a third wavelength between 770 nm and 1000 nm. The oxygen saturation measuring method and apparatus then measures the transmittance of the blood within the retinal vessel in response to the illumination at each of the selected wavelengths. Based upon the respective transmittances of the blood within the retinal vessel that are measured at each of the selected wavelengths, the oxygen saturation measuring method and apparatus determines the oxygen saturation of the blood within the retinal vessel. By appropriately selecting the combination of wavelengths with which the retinal vessel is illuminated, the corresponding error in the measured blood oxygen saturation can be reduced.

21 Claims, 5 Drawing Sheets

U.S. PATENT DOCUMENTS

| | | |
|---|---|---|
| 4,579,430 | 4/1986 | Bille . |
| 4,694,833 | 9/1987 | Hamaguri . |
| 4,697,593 | 10/1987 | Evans et al. . |
| 4,824,242 | 4/1989 | Frick et al. . |
| 4,836,207 | 6/1989 | Bursell et al. . |
| 4,838,683 | 6/1989 | Ichihashi et al. . |
| 4,859,056 | 8/1989 | Prosser et al. . |
| 4,869,254 | 9/1989 | Stone et al. . |
| 4,877,322 | 10/1989 | Hill . |
| 4,907,876 | 3/1990 | Suzuki et al. . |
| 4,922,919 | 5/1990 | Novack . |
| 4,941,741 | 7/1990 | Mizuta . |
| 4,942,877 | 7/1990 | Sakai et al. . |
| 5,078,136 | 1/1992 | Stone et al. . |
| 5,119,814 | 6/1992 | Minnich . |
| 5,219,400 | 6/1993 | Jacot et al. . |
| 5,246,002 | 9/1993 | Prosser . |
| 5,285,782 | 2/1994 | Prosser . |
| 5,297,554 | 3/1994 | Glynn et al. . |
| 5,308,919 | 5/1994 | Minnich . |
| 5,318,022 | 6/1994 | Taboada et al. . |
| 5,377,674 | 1/1995 | Kuestner . |
| 5,433,197 | 7/1995 | Stark . |
| 5,515,864 | 5/1996 | Zuckerman . |
| 5,517,987 | 5/1996 | Tsuchiya . |
| 5,524,617 | 6/1996 | Mannheimer . |

5,776,060

METHOD AND APPARATUS FOR MEASURING BLOOD OXYGEN SATURATION WITHIN A RETINAL VESSEL WITH LIGHT HAVING SEVERAL SELECTED WAVELENGTHS

BACKGROUND OF THE INVENTION

The present invention relates generally to methods and apparatus for measuring the blood oxygen saturation within a retinal vessel and, more particularly, to methods and apparatus for measuring blood oxygen saturation within a retinal vessel with light having several wavelengths selected to reduce the error associated with the oxygen saturation measurement.

A variety of spectroscopic oximetry techniques have been developed to monitor the blood oxygen saturation or blood oxygen content of the blood in retinal vessels. By monitoring the blood oxygen saturation, the arteriovenous oxygen difference can be determined as described by U.S. Pat. No. 5,308,919 to Thomas E. Minnich. Based upon the arteriovenous oxygen difference, the cardiac output of a patient can be determined in order to assist in post-operative monitoring and the management of critically ill patients. By monitoring the blood oxygen saturation, the loss of blood can also be detected and the rate and quantity of blood loss over time can be estimated as described in U.S. Pat. No. 5,119,814 to Thomas E. Minnich.

Conventional spectroscopic oximetry techniques measure the oxygen saturation of a blood sample by illuminating the blood sample with light having two or more different wavelengths and by measuring the intensity of the light which is transmitted and/or reflected by the blood sample. As known to those skilled in the art, the level of oxygen saturation of a blood sample directly affects the optical properties of the blood sample since desaturated hemoglobin transmits and reflects light in a quantitatively different manner than saturated hemoglobin, i.e. oxyhemoglobin. Based upon the measured intensity of the transmitted and/or reflected light, the conventional spectroscopic oximetry techniques can therefore determine the oxygen saturation of the blood sample.

Conventional spectroscopic oximetry techniques analyze blood which has been drawn from a patient and is disposed within a cuvette. Accordingly, the thickness of the sample and the concentration of the sample can be controlled to reduce the error in the measured blood oxygen saturation. In particular, O. W. Van Assendelft proposes in a book entitled *Spectrophotometry of Haemoglobin Derivatives* (Charles C. Thomas, Springfield, Ill. 1970) that the error in the measured blood oxygen saturation would be minimized if the errors in the relative optical density of the blood were minimized. Thus, for a blood sample having an optical density D, the relative optical density error is ΔD/D wherein ΔD is the absolute error in the optical density as measured. As described by Van Assendelft, the error in the measured blood oxygen saturation can be minimized by requiring the optical density of the blood sample to be 0.434 which, in turn, requires the optical transmittance of the blood sample to be 36.8%.

While the spectroscopic oximetry technique described by Van Assendelft is generally effective for reducing the error in the measured blood oxygen saturation, this technique requires blood to be drawn from a patient to be analyzed. To develop a time history of the blood oxygen saturation and to detect trends or changes in the blood oxygen saturation of a patient over time, this spectroscopic oximetry technique requires blood samples to be repeatedly drawn from a patient and analyzed. In addition to the discomfort of the patient from which the blood is drawn, it quickly becomes a laborious and time consuming task to repeatedly draw blood samples from a patient and then to analyze each of the samples to determine the blood oxygen saturation of the patient over time. In addition, the blood oxygen saturation of the patient cannot be analyzed in real time since the blood sample must be drawn and processed prior to measuring the blood oxygen saturation.

Accordingly, a number of non-invasive spectroscopic oximetry techniques have been developed to measure the blood oxygen saturation of a patient without requiring blood to be drawn from the patient. For example, a number of non-invasive spectroscopic oximetry techniques have been developed which measure the blood oxygen saturation of a patient based upon the transmittance of the blood within a retinal vein and/or a retinal artery. See, for example, U.S. Pat. No. 5,308,919 to Thomas E. Minnich which describes an eye oximeter for determining the arteriovenous oxygen difference by scanning the optic disk of a patient in a non-invasive manner. While these non-invasive spectroscopic oximetry techniques eliminate the drawing of blood from a patient, these non-invasive spectroscopic oximetry techniques cannot be readily optimized to measure the blood oxygen saturation in the most precise manner, i.e., to reduce the error in the measured blood oxygen saturation.

Since the blood which is analyzed during a non-invasive spectroscopic oximetry examination is contained within a blood vessel, such as retinal vein or retinal artery, the errors in the relative optical density and, in turn, the error in the measured blood oxygen saturation cannot be minimized in the same manner proposed by Van Assendelft for spectroscopic oximetry techniques designed to analyze a blood sample disposed within a cuvette. In particular, non-invasive spectroscopic oximetry techniques cannot control either the thickness of the blood sample, i.e., the thickness or diameter of the retinal vessel, or the concentration of the blood sample within the retinal vessel. As a result, the optical density of the blood sample analyzed by these non-invasive spectroscopic oximetry techniques will not generally be 0.434 and the corresponding transmittance of the blood sample will not generally be 36.8%. Thus, non-invasive spectroscopic oximetry techniques cannot be readily optimized to reduce the error in the measured blood oxygen saturation in the same manner as described above.

Conventional non-invasive spectroscopic oximetry techniques typically illuminate the retinal vessel with light having two or three different wavelengths, including at least one isobestic wavelength. Typically, the particular wavelengths of light with which the retinal vessel is illuminated are selected from among the wavelengths of light produced by commercially available light sources, such as commercially available lasers. As known to those skilled in the art, light having an isobestic wavelength is absorbed equally by both oxyhemoglobin and desaturated hemiglobin. Light having one or more isobestic wavelengths has historically been used in instances in which the absorption or extinction coefficients of a substance comprised of two components, each of which can be converted to the other, are not well-known. However, the millimolar extinction coefficients for oxyhemoglobin and desaturated hemoglobin are now well-known. As a result, spectroscopic oximetry techniques need not necessarily illuminate the retinal vessels with light having an isobestic wavelength to determine the blood oxygen saturation.

Several non-invasive spectroscopic oximeters have been designed to illuminate retinal vessels with light that includes not only an isobestic wavelength, but also a measurement wavelength selected such that the difference between the millimolar extinction coefficients for oxyhemoglobin and desaturated hemoglobin at the measurement wavelength is large. See F. C. Delori, *"Noninvasive Technique For Oximetry Of Blood In Retinal Vessels"*, Applied Optics, Vol. 27, No. 6, pp. 1113–25 (Mar. 15, 1988); A. J. Cohen and R. A. Laing, *"Multiple Scattering Analysis Of Retinal Blood Oximetry"*, IEEE Transactions On Biomedical Engineering, Vol. BME-23, No. 5, pp. 391–400 (September 1976); J. B. Hickman, et al., *"A Study Of Retinal Venous Blood Oxygen Saturation In Human Subjects By Photographic Means"*, Circulation, Vol. 27, pp. 375–84 (March 1963). It has been determined, however, that the illumination of a retinal vessel with light that includes a measurement wavelength selected such that the difference between the millimolar extinction coefficients for oxyhemoglobin and desaturated hemoglobin is large does not necessarily reduce or minimize measurement errors in the blood oxygen saturation.

As described above, a number of medical procedures demand that the blood oxygen saturation of a patient be accurately determined in a timely and efficient manner. While a number of invasive and non-invasive spectroscopic oximetry techniques have been developed for determining the blood oxygen saturation of a patient, a non-invasive spectroscopic oximetry technique for determining the blood oxygen saturation within a retinal vessel by illuminating the retinal vessel with light having a number of different wavelengths has not yet been developed which reduces or minimizes the error in the measured blood oxygen saturation.

SUMMARY OF THE INVENTION

It is therefore an object of the present invention to provide an improved method and apparatus for measuring the blood oxygen saturation within a retinal vessel in a non-invasive manner.

It is another object to the present invention to provide a method and apparatus for measuring the blood oxygen saturation of a patient with increased precision.

It is a further object of the present invention to provide a method and apparatus for measuring the blood oxygen saturation of a patient in a manner which reduces the effects of any measurement errors on the calculated blood oxygen saturation.

These and other objects are provided, according to the present invention, by a method and apparatus for measuring oxygen saturation of blood within a retinal vessel by illuminating the retinal vessel with light having a combination of wavelengths selected to reduce the error in the measured blood oxygen saturation. For example, the blood oxygen saturation measuring apparatus of the present invention can include a computer program product having a computer-readable storage medium including computer-readable program code means for facilitating the selection of a combination of wavelengths which reduces the error in the measured blood oxygen saturation.

Regardless of the implementation, the method and apparatus of the present invention illuminates a retinal vessel, such as with an optical source, with light having the selected combination of wavelengths. For example, in one particularly advantageous embodiment, the retinal vessel is illuminated with light having a first wavelength between 460 nm and 503 nm, a second wavelength between 600 nm, and 770 nm and a third wavelength between 770 nm and 1000 nm. The method and apparatus also measures, such as with a detector, the transmittance of the blood within the retinal vessel in response to the illumination at each of the selected wavelengths. Based upon the respective transmittances of the blood within the retinal vessel that are measured at each of the selected wavelengths, the method and apparatus of the present invention determines the oxygen saturation of the blood within the retinal vessel. By appropriately selecting the combination of wavelengths with which the retinal vessel is illuminated, the corresponding error in the measured blood oxygen saturation can be reduced.

According to the present invention, a relationship is initially determined between an error in the blood oxygen saturation measurement and measurement errors in the respective transmittances of the blood within the retinal vessel for light at a plurality of wavelengths. To determine this relationship, the method and apparatus of the present invention typically determines a relationship between the blood oxygen saturation of the retinal vessel and the respective transmittances of the blood within the retinal vessel for light at the plurality of wavelengths. According to one advantageous embodiment, the method and apparatus of the present invention determines the error $\Delta s$ in the blood oxygen saturation measurement as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)}$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

Based upon the relationship between the error in the blood oxygen saturation measurement and measurement errors in the respective transmittances of the blood within the retinal vessel for light at a plurality of wavelengths, the method and apparatus of the present invention can then determine, for each of a plurality of different combinations of wavelengths, the error in the oxygen saturation of the blood measurement for retinal vessels having a range of vessel diameters and for a range of blood oxygen saturation values. According to one advantageous embodiment, the method and apparatus of the present invention determines, for each of the plurality a different combination of wavelengths, the error in the blood oxygen saturation measurement arising from respective measurement errors in the transmittance of the blood within the retinal vessel for light at each of the different wavelengths.

Based upon the error in the blood oxygen saturation measurement, the method and apparatus of the present invention selects a combination of wavelengths to optimize the blood oxygen saturation measurement. Preferably, the method and apparatus of the present invention selects a combination of wavelengths which reduces or minimizes the error in the blood oxygen saturation measurement across a range of vessel diameters and a range of blood oxygen saturation values. As a result, the method and apparatus of the present invention can more precisely measure the blood oxygen saturation within a retinal vessel based upon the transmittance of the blood within a retinal vessel since a combination of wavelengths has been selected that reduces the errors in the measured blood oxygen saturation.

BRIEF DESCRIPTION OF THE DRAWINGS

Some of the objects and advantages of the present invention having been stated, others will appear as the description proceeds when taken in conjunction with the accompanying drawings, which are not necessarily drawn to scale, wherein.

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
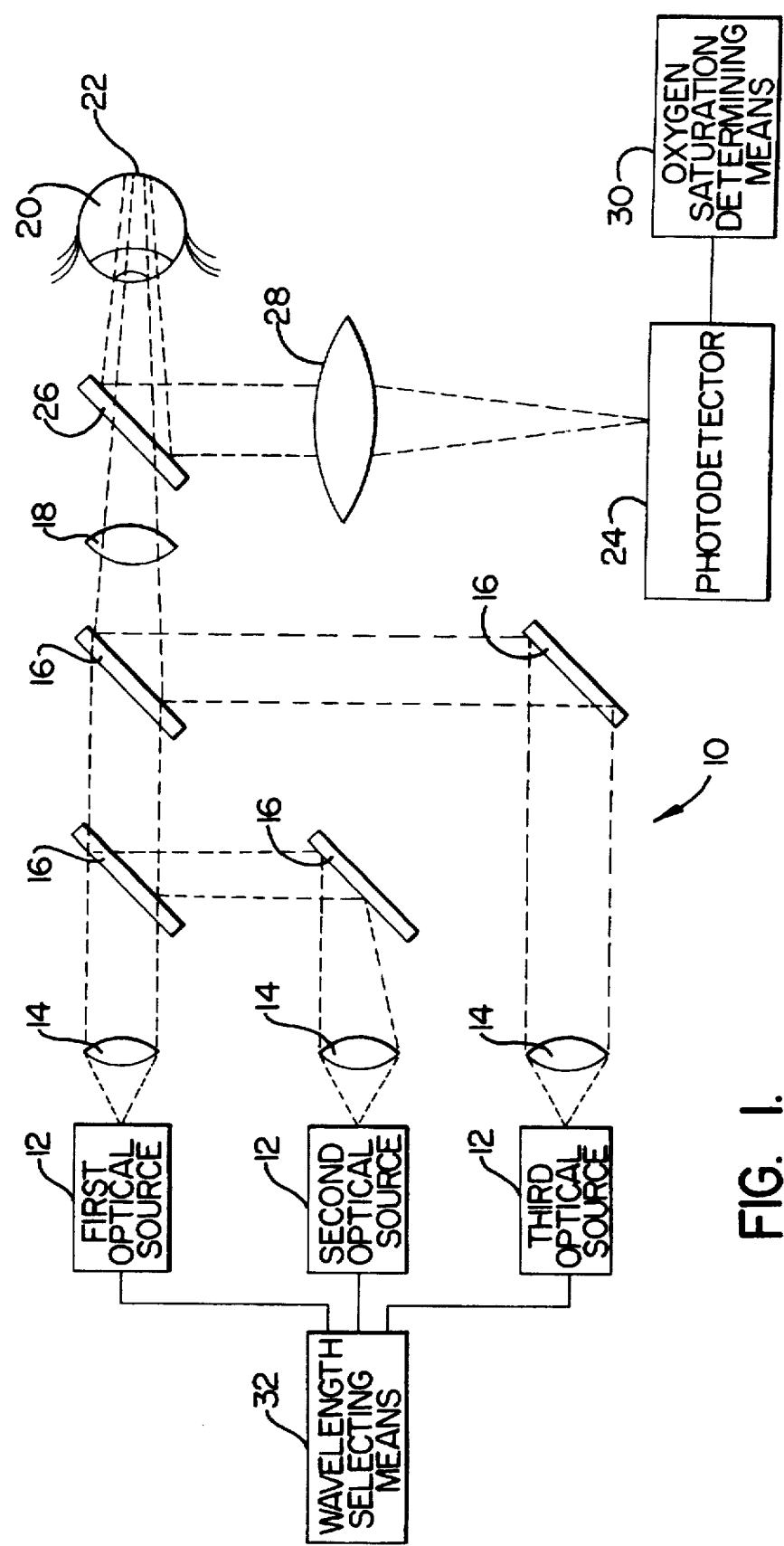
FIG. 1 is a block diagram illustrating one embodiment of the method and apparatus for measuring blood oxygen saturation within a retinal vessel according to the present invention.

Referring now to FIG. 1, an apparatus 10 for measuring the blood oxygen saturation within a retinal vessel with light having several selected wavelengths is illustrated. Based upon the measured blood oxygen saturation within a retinal vessel, physicians and other health care personnel can determine, among other things, changes during blood loss and/or changes in cardiac output.

As described hereinbelow, the method and apparatus 10 of the present invention measures the blood oxygen saturation within a retinal vessel based upon the respective transmittance of the retinal vessel at each of several selected wavelengths of light. Accordingly, the oxygen saturation measuring apparatus of the present invention includes an optical source 12 for illuminating a retinal vessel with light having a selected combination of wavelengths. Typically, the optical source illuminates the retinal vessel with light having either two or three different wavelengths. However, the optical source can illuminate the retinal vessel with light having any number of wavelengths without departing from the spirit and scope of the present invention. For purposes of illustration, however, FIG. 1 illustrates an oxygen saturation measuring apparatus according to one embodiment of the present invention which includes three optical sources, such as three lasers. Each optical source provides an optical signal having a different respective wavelength that has been selected in the manner described below.

The optical signals provided by each optical source are generally focused, such as by respective lens elements 14. In addition, the focused optical signals provided by each optical source are typically combined, such as by one or more beam combiners 16, to form a composite beam of light 18 having each of the different respective wavelengths.

As shown in FIG. 1, the composite beam of light 18 is directed so as to impinge upon a retinal vessel, such as a retinal vein and/or retinal artery. As known to those skilled in the art, the retina, including the retinal vessels, are disposed along the rear surface 22 of an eye 20. Accordingly, the method and apparatus 10 of the present invention illuminates the retina and, more particularly, the retinal vessels with the composite beam of light having the selected combination of wavelengths. As known to those skilled in the art, the blood within a retinal vessel typically absorbs and transmits light of each of the different wavelengths in a quantitatively different manner depending upon the level of oxygen saturation of the blood. In other words, oxyhemoglobin and unsaturated hemoglobin each absorb and reflect light of each of the different non-isobestic wavelengths in a different manner.

According to the present invention, the oxygen saturation measuring apparatus 10 includes a detector 24, such as a photodetector, for measuring the intensity of the light transmitted and/or reflected by the blood within the retinal vessel. In particular, the detector measures the intensity of the light at each respective wavelength to separately determine the light transmitted and reflected by the blood within the retinal vessel at each of the different wavelengths. As shown in FIG. 1, the oxygen saturation measuring apparatus can also include a beam splitter 26 and a focusing lens 28 to direct the light that has been transmitted and/or reflected by the blood within the retinal vessel to the photodetector. Based upon the intensity of the light provided by the respective optical sources at each of the different wavelengths and the intensity of the light detected by the detector at each of the different wavelengths, the method and apparatus of the present invention can readily determine the transmittance of the blood within the retinal vessel in response to illumination at each of the selected wavelengths.

As known to those skilled in the art, one mathematical model of the optical density D of blood can be expressed as follows:

$$D = cd[s\epsilon_{HbO_2} + (1-s)\epsilon_{Hb}] + D_0 \quad (1)$$

wherein $\epsilon_{HbO_2}$ is the millimolar extinction coefficient for oxyhemoglobin at a particular wavelength, $\epsilon_{Hb}$ is the millimolar extinction coefficient for unsaturated hemoglobin at a particular wavelength, c is the hemoglobin concentration of the blood, d is the vessel diameter or, more particularly, twice the vessel diameter since the light passes through the retinal vessel two times, and $D_0$ is a correction factor arising from scattering by red blood cells or other phenomena. For example, $D_0$ is 0 for a homogenous, non-scattering sample.

The oxygen saturation measuring apparatus 10 includes means for determining a relationship between the blood oxygen saturation s of the retinal vessel and the respective transmittances T of the blood within the retinal vessel for light at each of the different wavelengths. In particular, the relationship between the blood oxygen saturation s of the retinal vessel and the respective transmittances T of the blood within the retinal vessel for light at each of the different wavelengths can be derived from the relationship between the optical density D and the blood oxygen saturation s set forth in Equation 1 as follows:

$$D = -\log T \quad (2)$$

For example, by assuming that $D_0$ is a constant, the relationship between the blood oxygen saturation s of the retinal vessel and the respective transmittances T of the blood within the retinal vessel for light at each of the different wavelengths can be set forth as follows:

$$s = \frac{-\log T^{\lambda_1}(\epsilon_{Hb}^{\lambda_2} - \epsilon_{Hb}^{\lambda_3}) - \log T^{\lambda_2}(\epsilon_{Hb}^{\lambda_1} - \epsilon_{Hb}^{\lambda_3}) - \log T^{\lambda_3}(\epsilon_{Hb}^{\lambda_2} - \epsilon_{Hb}^{\lambda_1})}{-\log T^{\lambda_1}[(\epsilon_{Hb}^{\lambda_2} - \epsilon_{HbO_2}^{\lambda_2}) - (\epsilon_{Hb}^{\lambda_3} - \epsilon_{HbO_2}^{\lambda_3})] - \log T^{\lambda_2}[(\epsilon_{Hb}^{\lambda_1} - \epsilon_{HbO_2}^{\lambda_1}) - (\epsilon_{Hb}^{\lambda_3} - \epsilon_{HbO_2}^{\lambda_3})] - \log T^{\lambda_3}[(\epsilon_{Hb}^{\lambda_2} - \epsilon_{HbO_2}^{\lambda_2}) - (\epsilon_{Hb}^{\lambda_1} - \epsilon_{HbO_2}^{\lambda_1})]} \quad (3)$$

wherein superscripts $\lambda_1$, $\lambda_2$ and $\lambda_3$ specify the wavelength at which certain wavelength-specific parameters, such as transmittances T and millimolar extinction coefficients $\epsilon$, are determined. Although the relationship between the blood oxygen saturation of a retinal vessel and the respective transmittances of the blood within a retinal vessel for light at the different wavelengths is set forth in Equation 3 for light having three different wavelengths, namely, $\lambda_1$, $\lambda_2$ and $\lambda_3$, the relationship between the blood oxygen saturation of the retinal vessel and the respective transmittances of the blood within a retinal vessel can be expanded for light having more than three different wavelengths, if so desired, and can be simplified for light having only two different wavelengths. For example, by assuming that $D_0$ is 0, Equation 3 can be rewritten as follows:

$$s = \frac{\log(T^{\lambda_2})\epsilon_{Hb}^{\lambda_1} - \log(T^{\lambda_1})\epsilon_{Hb}^{\lambda_2}}{\log(T^{\lambda_1})(\epsilon_{HbO_2}^{\lambda_2} - \epsilon_{Hb}^{\lambda_2}) - \log(T^{\lambda_2})(\epsilon_{HbO_2}^{\lambda_1} - \epsilon_{Hb}^{\lambda_1})} \quad (4)$$

While $D_0$ has been set equal to a constant, including 0, in order to construct Equations 3 and 4, $D_0$ may vary with respect to the wavelength of light with which the retinal vessel is illuminated. Alternatively, $D_0$ may vary with respect to both the wavelength of light with which the retinal vessel is illuminated and the diameter of the retinal vessel. As known to those skilled in the art, however, other equations could be constructed in instances in which $D_0$ varies so as to describe the relationship between blood oxygen saturation s and the respective transmittances T of the blood within the retinal vessel at each of the selected wavelengths of light.

As illustrated in FIG. 1, the oxygen saturation measuring apparatus 10 of one advantageous embodiment of the present invention therefore includes means 30 for determining the blood oxygen saturation within a retinal vessel based upon the respective transmittances of the blood within a retinal vessel, as measured by the detector 24, at each of the selected wavelengths.

According to the present invention, the oxygen saturation apparatus 10 also includes means 32 for selecting a combination of wavelengths of light based upon a corresponding error in the blood oxygen saturation measurement. As set forth in more detail in blocks 40 and 42 of the flow chart of FIG. 6, the method and apparatus for measuring blood oxygen saturation within a retinal vessel according to the present invention initially determines a relationship between an error in the blood oxygen saturation measurement and measurement errors in the respective transmittances of the blood within the retinal vessel for light at each of a plurality of different wavelengths. Typically, the relationship between the error in the blood oxygen saturation measurement and the measurement errors in the respective transmittances of the blood within the retinal vessel for light at each of the plurality of different wavelengths is based upon the above-described relationship between the blood oxygen saturation of the retinal vessel and the respective transmittances of the blood within the retinal vessel for light at each of the different wavelengths, such as set forth in Equations 3 and 4 for light having three different wavelengths and two different wavelengths, respectively.

In particular, the method and apparatus 10 of one advantageous embodiment of the present invention can determine the error in the calculated blood oxygen saturation within the retinal vessel as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)} \quad (5)$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

For the embodiment of the method and apparatus 10 of the present invention in which the optical source provides light having two different wavelengths, namely, $\lambda_1$ and $\lambda_2$, the relationship between the error in the blood oxygen saturation measurement and the measurement errors in the respective transmittances of the blood within the retinal vessel for light at each of the two different wavelengths can be reduced to:

$$\Delta s = \sqrt{\left(\frac{\partial s}{\partial T^{\lambda_1}} \cdot \Delta T^{\lambda_1}\right)^2 + \left(\frac{\partial s}{\partial T^{\lambda_2}} \cdot \Delta T^{\lambda_2}\right)^2} \quad (6)$$

As will be apparent to those skilled in the art, the partial derivatives of the blood oxygen saturation s within a retinal vessel with respect the transmittance T of the blood within the retinal vessel to light having a respective one of the wavelengths can be determined based upon the above-described relationship between the blood oxygen saturation within a retinal vessel and the transmittance of the blood within the retinal vessel to light having several different wavelengths. For example, with respect to the embodiment of the method and apparatus 10 of the present invention in which the optical source 12 provides light having two different wavelengths, namely, $\lambda_1$ and $\lambda_2$, the partial derivative of the blood oxygen saturation s within a retinal vessel with respect to the transmittance T of the blood within the retinal vessel to light having the first and second wavelengths can be described as follows:

$$\frac{\partial s}{\partial T^{\lambda_1}} = -\frac{\log(T^{\lambda_2})}{T^{\lambda_1}} \cdot \frac{\epsilon_{Hb}^{\lambda_1}\epsilon_{HbO_2}^{\lambda_2} - \epsilon_{Hb}^{\lambda_2}\epsilon_{HbO_2}^{\lambda_1}}{[\log(T^{\lambda_1}) \cdot (\epsilon_{HbO_2}^{\lambda_2} - \epsilon_{Hb}^{\lambda_2}) - \log(T^{\lambda_2}) \cdot (\epsilon_{HbO_2}^{\lambda_1} - \epsilon_{Hb}^{\lambda_1})]^2} \quad (7)$$

$$\frac{\partial s}{\partial T^{\lambda_2}} = -\frac{\log(T^{\lambda_1})}{T^{\lambda_2}} \cdot \frac{\epsilon_{Hb}^{\lambda_2}\epsilon_{HbO_2}^{\lambda_1} - \epsilon_{Hb}^{\lambda_1}\epsilon_{HbO_2}^{\lambda_2}}{[\log(T^{\lambda_2}) \cdot (\epsilon_{HbO_2}^{\lambda_1} - \epsilon_{Hb}^{\lambda_1}) - \log(T^{\lambda_1}) \cdot (\epsilon_{HbO_2}^{\lambda_2} - \epsilon_{Hb}^{\lambda_2})]^2}$$

Figure 6:
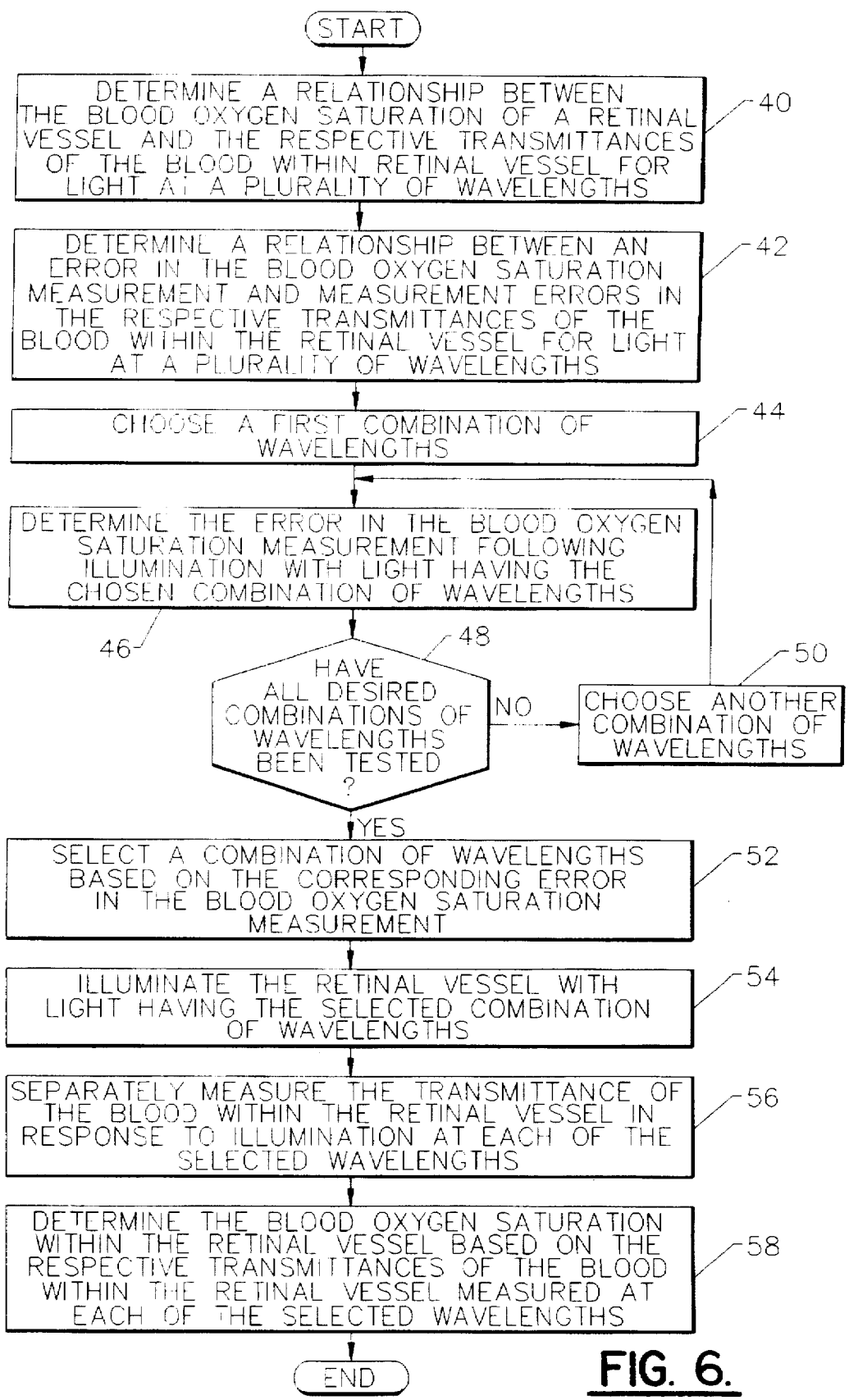
FIG. 6 is a flow chart illustrating the operations performed by one embodiment of the method and apparatus for measuring blood oxygen saturation within a retinal vessel according to the present invention.

As shown in blocks 44–50 of FIG. 6, the method and apparatus 10 for measuring blood oxygen saturation within a retinal vessel also determines, for each of a plurality of different combinations of wavelengths, the error in the blood oxygen saturation measured within a retinal vessel for retinal vessels having a range of vessel diameters and a range of blood oxygen saturation values. As described above, the blood oxygen saturation within a retinal vessel and, in turn, the error in the blood oxygen saturation measurement is dependent upon several parameters. In particular, the error in the blood oxygen saturation measurement is dependent upon the hemoglobin concentration c, the retinal vessel diameter d, the measurement error $\Delta T^{\lambda}$ in the respective transmittances of the blood within the retinal vessel for light at each of the different wavelengths, and the actual blood oxygen saturation s within the retinal vessel.

To more efficiently determine the error in the blood oxygen saturation measured within a retinal vessel, the hemoglobin concentration c, the measurement error $\Delta T^{\lambda}$ in the respective transmittances of the blood within the retinal vessel for light at each of the different wavelengths, and the vessel diameter d are typically set to predetermined values which approximate the actual measurement conditions. For example, the hemoglobin concentration c can be set to 15 $g_{Hb}/100$ $ml_{blood}$. In addition, the measurement error $\Delta T^{\lambda}$ in the respective transmittances of the blood within the retinal vessel for light at each of the different wavelengths can be set equal to a predetermined value, such as 0.01 which represents a 1% measurement error in the respective transmittances of the blood within the retinal vessels, at each of the different wavelengths. Finally, the vessel diameter d can be set equal to 100 μm which equals two passes through a retinal vessel having an actual diameter of 50 μm.

To select an appropriate combination of wavelengths for reliably measuring the blood oxygen saturation within a retinal vessel, the method and apparatus 10 for measuring blood oxygen saturation within a retinal vessel according to the present invention can determine the error in the blood oxygen saturation measured within the retinal vessel for each of a plurality of different combinations of wavelengths by repeating the steps described above. Based upon the error in the blood oxygen saturation measured within a retinal vessel for each of a plurality of different combinations of wavelengths, the wavelength selecting means 32 can select a combination of wavelengths that reduces the error in the blood oxygen saturation measurement. See block 52 of FIG. 6. Since the millimolar extinction coefficients are known for both oxyhemoglobin and desaturated hemoglobin, the wavelength selecting means need not select an isobestic wavelength, but, instead, the wavelength selecting means can select any combination of wavelengths which reduces the corresponding error in the measured blood oxygen saturation.

To expedite the wavelength selection process, the wavelength selecting means 32 of one advantageous embodiment can specify, in advance, one or more of the wavelengths of light. For example, the wavelength selection means can specify the predetermined wavelength(s) of light based upon the wavelengths of light emitted by commercially available lasers and/or based upon the wavelengths of light that have been employed previously to measure the blood oxygen saturation of the retinal vessel. According to the present invention, however, the wavelength selecting means selects at least one of the wavelengths of light based upon the corresponding error in the measured blood oxygen saturation. In particular, the wavelength selecting means preferably selects at least one of the wavelengths of light to reduce or minimize the corresponding error in the measured blood oxygen saturation.

In one embodiment of the present invention in which the optical source 12 provides light 18 having two different wavelengths, the wavelength selecting means 32 can specify one of the wavelengths of light in advance. For example, the wavelength selecting means can specify that the optical source provide light having a wavelength of 670 nm. The method and apparatus 10 of the present invention can then determine the respective error in the blood oxygen saturation measured within the retinal vessel when illuminated by light having a first wavelength of 670 nm and each of a number of different second wavelengths. Although the wavelength selecting means need not impose any limits on the second wavelength, the second wavelength typically varies between 450 nm and 1000 nm.

Figure 2:
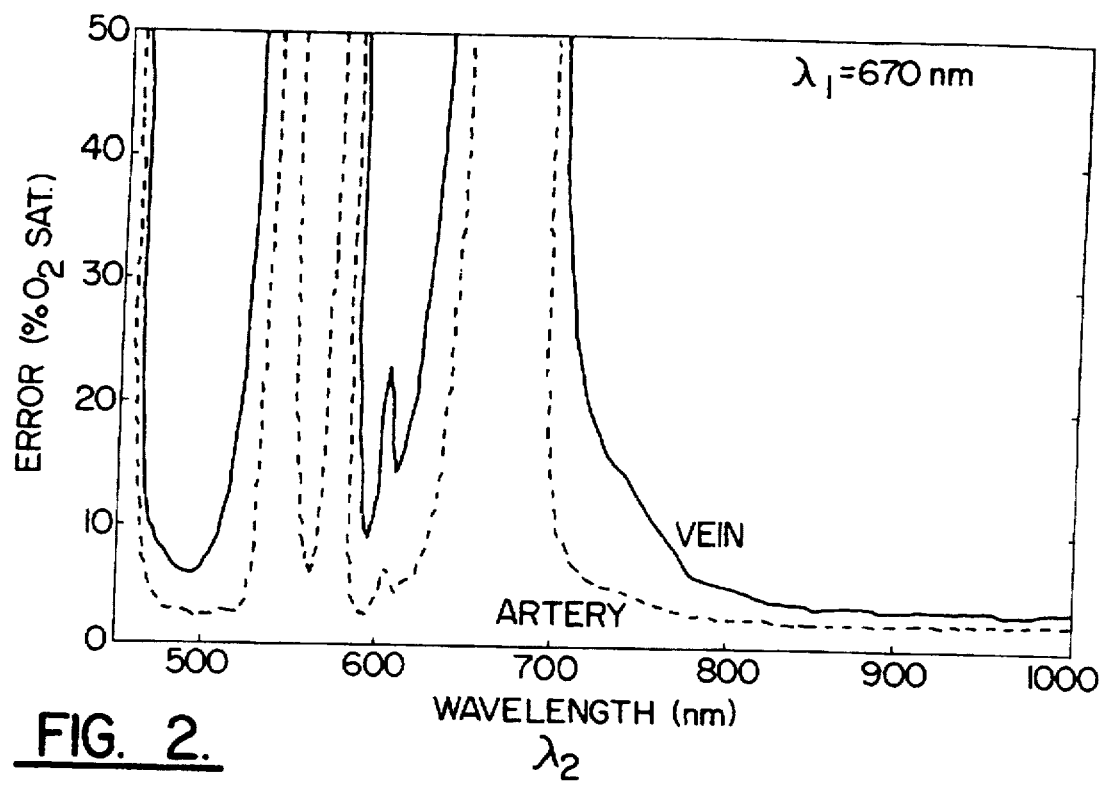
FIG. 2 is a graph illustrating the error in the measured blood oxygen saturation of both retinal veins and retinal arteries as a function of the wavelength of light with which the retinal vessels are illuminated.

As depicted in FIG. 2, the error in the blood oxygen saturation measured within the retinal vessel when illuminated by light having a first wavelength of 670 nm and each of a number of second wavelengths between 450 nm and 1000 nm is plotted as a function of the second wavelength of light. As described above, the error in the blood oxygen saturation measurement is dependent upon a number of other parameters, including the hemoglobin concentration c, the vessel diameter d, the actual blood oxygen saturation s within the retinal vessel, and the error $\Delta T^{\lambda}$ in the respective transmittances of the blood within the retinal vessel at each of the different wavelengths. With respect to the relationship depicted in FIG. 2, therefore, the hemoglobin concentration is set equal to 15 $g_{Hb}/100$ $ml_{blood}$ and the measurement error $\Delta T^{\lambda}$ in the respective transmittances of the blood within the retinal vessel at each of the different wavelengths is set equal to 0.01.

As shown in FIG. 2, the error in the blood oxygen saturation measured within a retinal vessel is depicted as a function of the second wavelength for both retinal veins and retinal arteries. In order to separately determine the error in the blood oxygen saturation as a function of the second wavelength, several of the parameters that define the retinal vessels are set to different values for retinal veins and for retinal arteries. With respect to FIG. 2, therefore, the diameter of the retinal vessel is set equal to 150 μm for a retinal artery and 200 μm for a retinal vein. In addition, the actual blood oxygen saturation is set equal to 98% for a retinal artery and 50% for a retinal vein.

Preferably, the method and apparatus 10 for measuring blood oxygen saturation within a retinal vessel according to the present invention selects a combination of wavelengths which reduces the corresponding error in the measured blood oxygen saturation. As set forth below in Table I, the respective errors As in the blood oxygen saturation within a retinal vessel and a retinal vein graphically depicted in FIG. 2 are provided for several combinations of wavelengths which provide relatively small errors in the measured blood oxygen saturation for both retinal veins and retinal arteries.

TABLE I

| Wavelengths (nm) | Arterial Error, ΔS (% O₂Sat.) | Venous Error, ΔS (% O₂Sat.) |
|---|---|---|
| 670,492 | 2.61% | 5.95% |
| 670,590 | 3.03% | 9.07% |
| 670,803 | 2.79% | 5.19% |
| 670,960 | 2.46% | 3.37% |

As described above, the error in the measured blood oxygen saturation depicted in FIG. 2 was determined for blood having a predetermined blood oxygen saturation and for vessels of a predetermined diameter. In order to further optimize the wavelength selection process, the method and apparatus 10 of the present invention can initially identify those combinations of wavelengths which produced relatively small errors in the measured blood oxygen saturation for both retinal veins and retinal arteries (see Table 1) and can thereafter determine, for each of these combinations of wavelengths, the respective error in the blood oxygen saturation measurement at each of a number of different levels of blood oxygen saturation s and for vessels having each of a number of different diameters. For example, this step of determining the error in the blood oxygen saturation measurement obtained by illumination of the retinal vessel with light having a particular combination of wavelengths at a number of different levels of blood oxygen saturation can be repeated for retinal vessels having different diameters, such as 100 μm, 150 μm, 200 μm and 250 μm.

Figure 3:
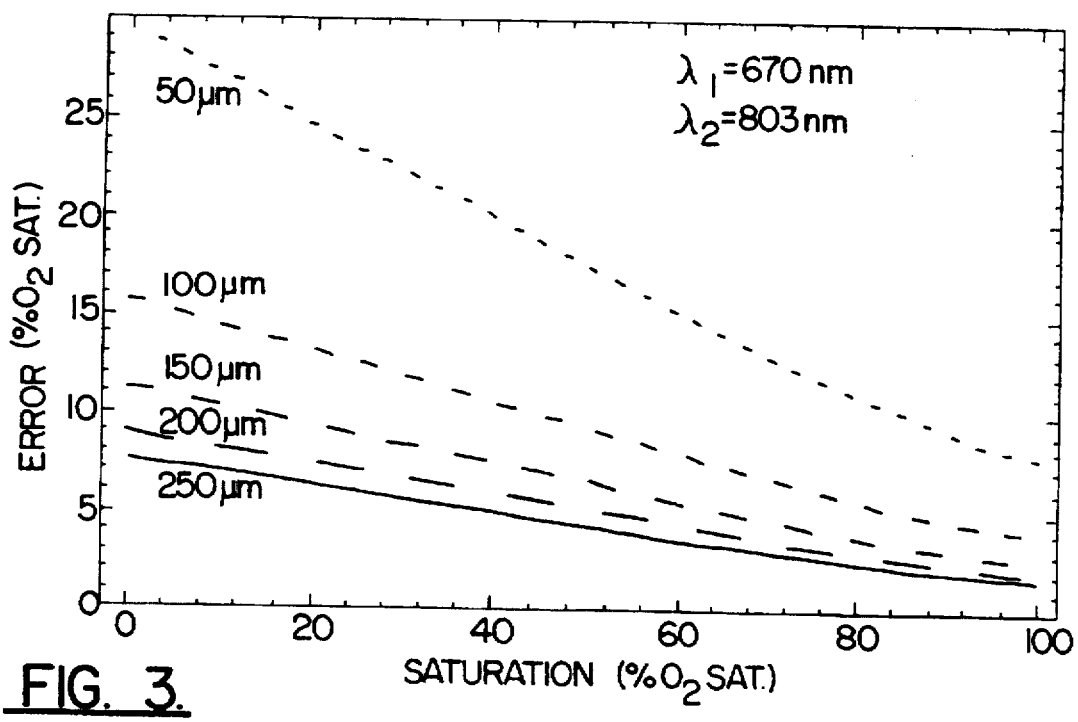
FIG. 3 is a graph illustrating the error in the measured blood oxygen saturation as a function of the actual blood oxygen saturation levels of retinal vessels having a number of different diameters based upon illumination of the retinal vessels with light having wavelengths of 670 nm and 803 nm.

By way of illustration, FIG. 3 provides a graphical representation of the error in the blood oxygen saturation measured within a retinal vessel as a function of the actual blood oxygen saturation within the retinal vessel for vessels having several different diameters. As indicated in FIG. 3, the graph was constructed based upon the respective transmittance of the blood within the retinal vessel to light having wavelengths of 670 nm and 803 nm. In addition, the hemoglobin concentration c was set equal to 15 $g_{Hb}/100$ $ml_{blood}$ and the measurement error $\Delta T^{\lambda_i}$ in the respective transmittances of the blood within the retinal vessel to light at each of the different wavelengths is set equal to 0.01.

The method and apparatus 10 for measuring the blood oxygen saturation within a retinal vessel preferably selects a combination of wavelengths such that the corresponding error in the measured blood oxygen saturation within both the retinal veins and the retinal arteries is no greater than a predetermined maximum error, such as 10%, across the range of vessel diameters and the range of blood oxygen saturation values. As a result, light having any of the combinations of wavelengths set forth in Table I would generally be acceptable since the corresponding error in the measured blood oxygen saturation within both the retinal veins and retinal arteries is less than 10% for vessels having normal diameters and for typical blood oxygen saturation levels. Although not illustrated, it has been determined that blood oxygen saturation measurements obtained by a spectroscopic oximetry apparatus that illuminates a retinal vessel with light having two wavelengths can be optimized by selecting the wavelengths to be 605 nm and 960 nm.

Figure 4:
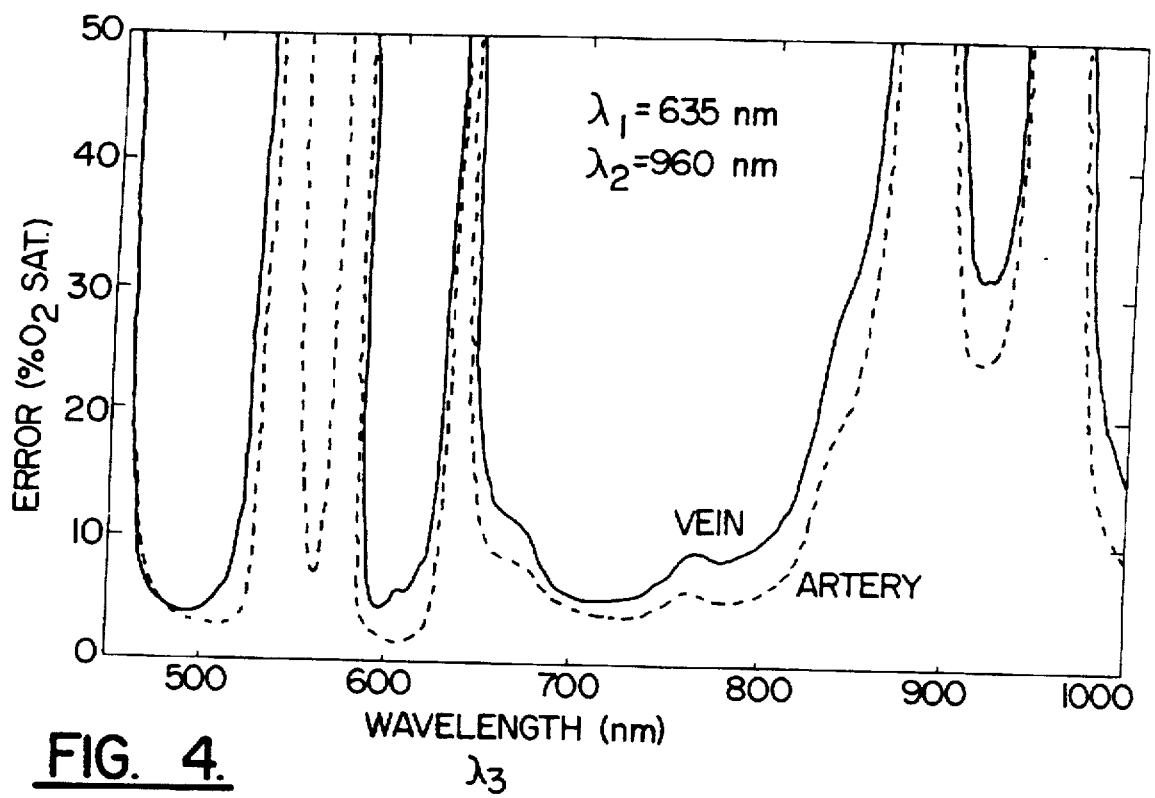
FIG. 4 is another graph illustrating the error in the measured blood oxygen saturation of both retinal veins and retinal arteries as a function of the wavelength of light with which the retinal vessels are illuminated.

While described above in conjunction with an optical source 12 which illuminates a retinal vessel with light having two wavelengths, the method and apparatus 10 for measuring blood oxygen saturation within a retinal vessel can be readily expanded to include optical sources which illuminate the retinal vessel with light having three or more different wavelengths. In this regard, FIG. 4 illustrates the error in the measured blood oxygen saturation within the retinal vessel for retinal vessels illuminated with light having a first wavelength of 635 nm, a second wavelength of 960 nm and a variable third wavelength as a function of the third wavelength. In a like manner to that described above, the relationship depicted in FIG. 4 was determined based upon a hemoglobin concentration of 15 $g_{Hb}/100$ $ml_{blood}$, and respective measurement errors $\Delta T^{\lambda_i}$ in the transmittances of the blood within the retinal vessel at each of the different wavelengths of 0.01. As described above in conjunction with FIG. 2, FIG. 4 depicts the error in the measured blood oxygen saturation as a function of the third wavelength for both retinal veins and retinal arteries. Thus, the actual blood oxygen saturation s is set equal to 98% for retinal arteries and 50% for retinal veins, and the vessel diameter d is set equal to 150 nm for retinal arteries and 200 nm for retinal veins. By way of further illustration, Table II sets forth the respective errors in the blood oxygen saturation measured within a retinal artery and a retinal vein for a number of different combinations of wavelengths along with a description of the particular relevance of the corresponding wavelength combination.

TABLE II

| Wavelengths (nm) | Arterial Error, Δs (% O₂Sat.) | Venous Error, Δs (% O₂Sat.) | Description |
|---|---|---|---|
| 635,496,922 | 3.95% | 3.61% | local minimum for vein |
| 635,721,960 | 4.64% | 3.91% | local minimum for vein; commercially available alternative |
| 635,597,922 | 4.43% | 2.14% | local minimum for vein |
| 635,492,605 | 6.85% | 2.90% | local minimum for vein |
| 635,605,960 | 5.74% | 1.56% | local minimum for artery |
| 635,495,605 | 7.00% | 2.81% | local minimum for artery |
| 670,496,917 | 3.56% | 4.41% | local minimum for vein |
| 670,496,670 | 7.11% | 2.72% | local minimum for vein |
| 670,598,908 | 4.11% | 2.09% | local minimum for vein |
| 670,505,605 | 9.68% | 2.69% | local minimum for artery |
| 670,592,605 | 13.69% | 2.77% | local minimum for artery |
| 635,670,960 | 11.28% | 8.15% | commercially available alternative |
| 635,803,960 | 9.99% | 5.58% | commercially available alternative |
| 670,803,960 | 9.49% | 10.24% | commercially available alternative |

As illustrated in FIG. 4 and depicted in Table II, a number of different combinations of wavelengths can be selected to ensure that a corresponding error in the blood oxygen saturation measured within both the retinal veins and the retinal arteries is no greater than a predetermined percentage, such as 10%. In order to optimize the wavelength selection process, several combinations of wavelengths which produce relatively low errors in the measured blood oxygen saturation can be identified from the results presented in FIG. 4 for further investigation. For example, FIG. 4 indicates that wavelength triads of 493, 635 & 960 nm; 595, 635 & 960 nm; and 635, 720 & 960 nm produce the smallest errors in the measured blood oxygen saturation.

Figure 5A:
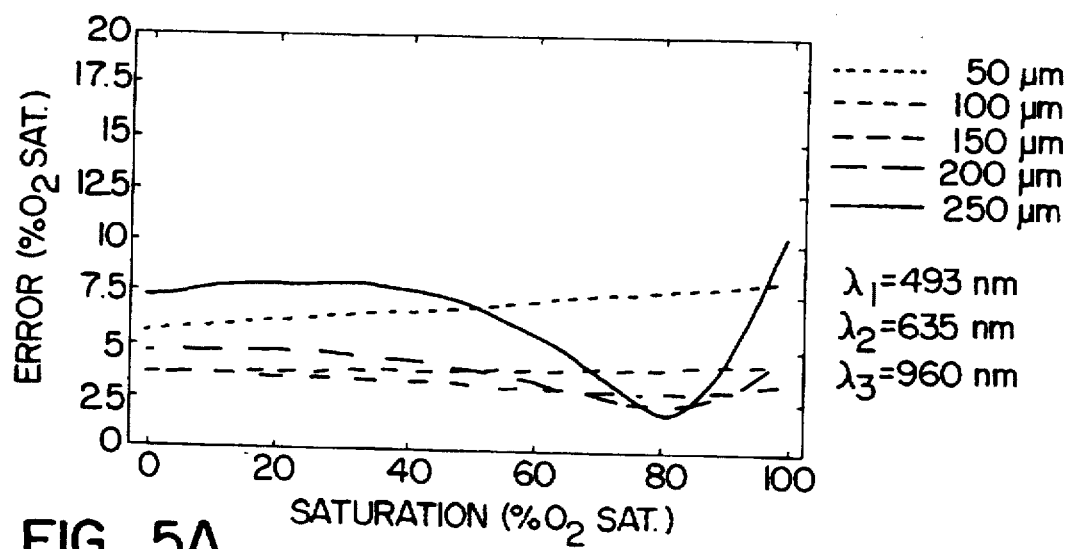
FIGS. 5A–5C are graphs illustrating the error in the measured blood oxygen saturation as a function of the actual blood oxygen saturation levels of retinal vessels having a number of different diameters based upon illumination of the retinal vessels with light having three different combinations of wavelengths.
Figure 5B:
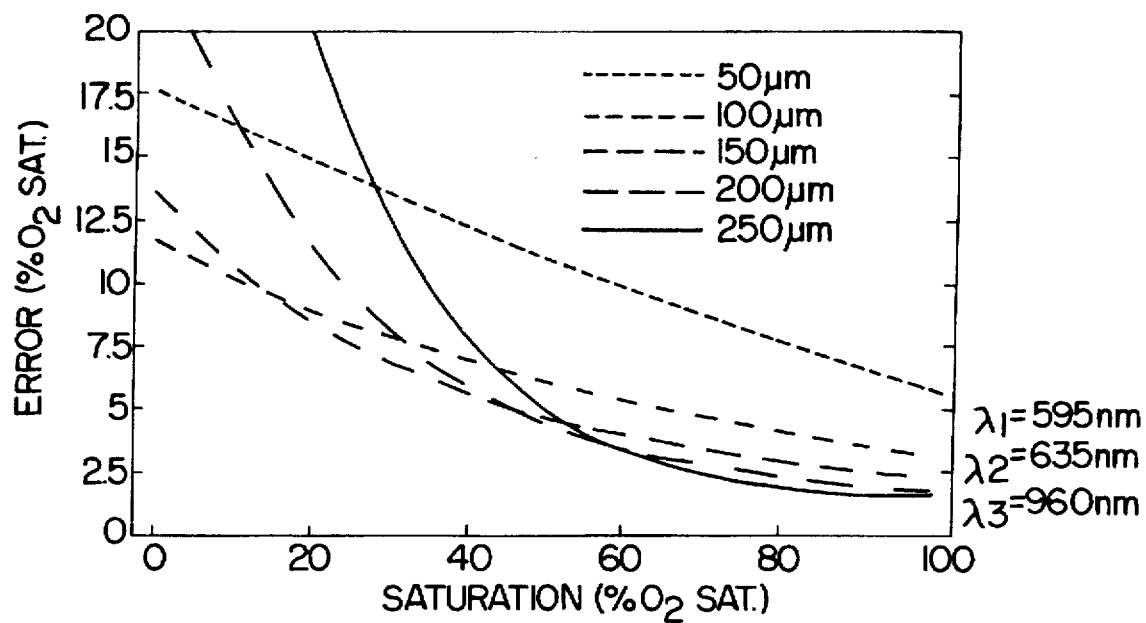
Figure 5C:
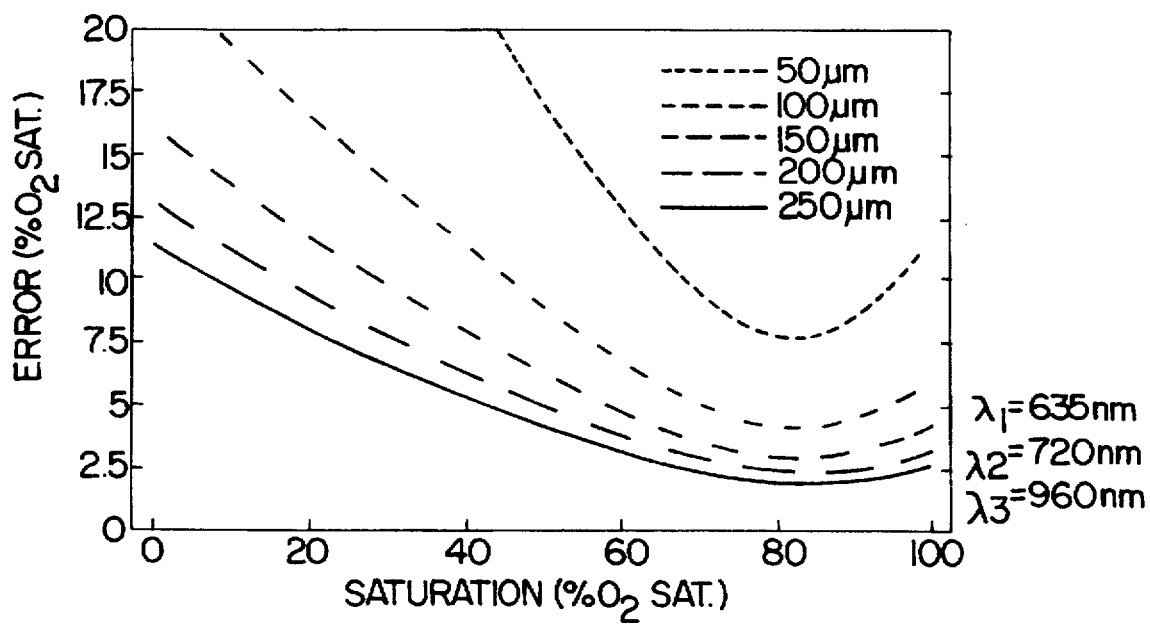

Accordingly, the errors in the measured blood oxygen saturation produced by each of these wavelength triads can be further investigated by determining, for each wavelength triad, the respective error in the measured blood oxygen saturation as a function of blood oxygen saturation and vessel diameter. In this regard, FIGS. 5A–5C illustrate the error in the blood oxygen saturation measurement as a function of actual blood oxygen saturation for retinal vessel of several diameters which are illuminated by light having the wavelength triads of 493, 635 & 960 nm; 595, 635 & 960 nm; and 635, 720 & 960 nm, respectively. In the embodiment illustrated in FIGS. 5A–5C, the hemoglobin concentration is 15 $g_{Hb}/100\ ml_{blood}$ and the measurement error $\Delta T^{\lambda_i}$ in the respective transmittances of the blood within the retinal vessel for light at each of the different wavelengths is 0.01.

By analyzing the resulting errors in blood oxygen saturation measurements as described above for a variety of wavelength combinations, it has been determined that blood oxygen saturation measurements obtained by a spectroscopic oximetry apparatus that illuminates a retinal vessel with light having three wavelengths can be optimized by selecting the first wavelength to be between 460 nm and 503 nm, the second wavelength to be between 600 nm and 770 nm and the third wavelength to be between 770 nm and 1000 nm. Within these ranges of wavelengths, it has been determined that errors in blood oxygen saturation measurements can be significantly reduced by illuminating the retinal vessel with light having a wavelength triad of 493 nm, 635 nm and 960 nm. See, for example, FIG. 5A which depicts relatively small errors in the blood oxygen saturation measurements across a wide range of actual blood oxygen saturations and over a wide range of vessel diameters, particularly in comparison with the larger errors in the blood oxygen saturation measurements illustrated by FIGS. 5B and 5C over the same ranges.

Once the wavelength selecting means 32 has selected an appropriate combination of wavelengths, the optical source 12 can illuminate the retinal vessel and the photodetector 24 can measure the respective transmittances of the blood within the retinal vessel at each of the selected wavelengths as shown in blocks 54 and 56 in FIG. 6. Based upon the measured transmittances, the oxygen saturation determining means 30 can precisely determine the blood oxygen saturation within the retinal vessel as shown in block 58 of FIG. 6.

By selecting a combination of wavelengths which reduces or minimizes the error in the blood oxygen saturation measurement, such as to less than 10% across the range of vessel diameters and the range of blood oxygen saturation values, the method and apparatus 10 of the present invention can more precisely measure the blood oxygen saturation within the retinal vessel based upon the transmittance of the retinal vessel at each of the selected wavelengths. Thus, physicians and other health care professionals will be able to obtain more precise data relating to a patient's blood oxygen saturation to more precisely diagnose or treat the patient.

In one advantageous embodiment, portions of the method and apparatus 10 of the present invention, such as the wavelength selecting means 32 and the oxygen saturation determining means 30, include a computer program product. The computer program product includes a computer-readable storage medium having computer-readable program code means, such as a series of computer instructions, embodied in the computer-readable storage medium for measuring the transmittance of blood within a retinal vessel based upon the intensity signals.

In this regard, FIGS. 1 and 6 are block diagram, flowchart and control flow illustrations of methods, systems and program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions. Many modifications and other embodiments of the invention will come to mind to one skilled in the art to which this invention pertains having the benefit of the teachings presented in the foregoing descriptions and the associated drawings.

Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method of measuring blood oxygen saturation within a retinal vessel based upon a transmittance of the blood within the retinal vessel, the method comprising the steps of:

determining a relationship between an error in a blood oxygen saturation measurement and measurement errors in the respective transmittances of the blood within the retinal vessel for light at a plurality of wavelengths;

determining, for each of a plurality of different combinations of wavelengths, the error in the blood oxygen saturation measurement for retinal vessels having a range of vessel diameters and a range of blood oxygen saturation values;

selecting a combination of wavelengths based upon the corresponding error in the blood oxygen saturation measurement;

illuminating the retinal vessel with light having the selected combination of wavelengths;

measuring the transmittance of the blood within the retinal vessel in response to illumination at each of the selected wavelengths; and determining the blood oxygen saturation within the retinal vessel based upon the respective transmittances of the blood within the retinal vessel measured at each of the selected wavelengths.

2. A method according to claim 1 wherein said step of determining a relationship comprises the step of determining a relationship between the blood oxygen saturation of the retinal vessel and the respective transmittances of the blood within the retinal vessel for light at the plurality of wavelengths.

3. A method according to claim 1 wherein said step of determining a relationship comprises the step of determining the error Δs in the blood oxygen saturation measurement as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)}$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

4. A method according to claim 3 wherein said step of determining the error in the blood oxygen saturation measurement comprises the step of determining, for each of the plurality of different combinations of wavelengths, the error in the blood oxygen saturation measurement arising from respective measurement errors $\Delta T^{\lambda_n}$ in the transmittance of the blood within the retinal vessel for light at each of the different wavelengths.

5. A method according to claim 4 wherein said step of determining the error in the blood oxygen saturation measurement comprises the step of setting the predetermined transmittance error to a constant value for light having each of the different wavelengths.

6. A method according to claim 4 wherein said step of determining the error in the blood oxygen saturation measurement comprises the step of setting the predetermined transmittance error to a value which varies for light having different wavelengths.

7. A method of selecting a combination of wavelengths of light to reduce errors in measuring blood oxygen saturation within a retinal vessel based upon a transmittance of the retinal vessel, the method comprising the steps of:

determining a relationship between an error in a blood oxygen saturation measurement and measurement errors in the respective transmittances of the blood within the retinal vessel for light at a plurality of wavelengths;

determining, for each of a plurality of different combinations of wavelengths, the error in the blood oxygen saturation measurement for retinal vessels having a range of vessel diameters and a range of blood oxygen saturation values; and selecting a combination of wavelengths based upon the corresponding error in the blood oxygen saturation measurement, wherein said selecting step comprises selecting a combination of wavelengths such that the corresponding error in the blood oxygen saturation measurement is no greater than a predetermined maximum error across the range of vessel diameters and the range of blood oxygen saturation values.

8. A method according to claim 7 wherein said step of determining a relationship comprises the step of determining a relationship between the blood oxygen saturation of the retinal vessel and the respective transmittances of the blood within the retinal vessel for light at the plurality of wavelengths.

9. A method according to claim 7 wherein said step of determining a relationship comprises the step of determining the error Δs in the blood oxygen saturation measurement as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)}$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

10. A method according to claim 9 wherein said step of determining the error in the blood oxygen saturation measurement comprises the step of determining, for each of the plurality of different combinations of wavelengths, the error in the blood oxygen saturation measurement arising from respective measurement errors $\Delta T^{\lambda_n}$ in the transmittance of the blood within the retinal vessel for light at each of the different wavelengths.

11. A method according to claim 10 wherein said step of determining the error in the blood oxygen saturation measurement comprises the step of setting the predetermined transmittance error to a constant value for light having each of the different wavelengths.

12. A method according to claim 10 wherein said step of determining the error in the blood oxygen saturation measurement comprises the step of setting the predetermined transmittance error to a value which varies for light having different wavelengths.

13. A computer program product for facilitating a selection of a combination of wavelengths of light to reduce errors in measuring blood oxygen saturation within a retinal vessel based upon a transmittance of the retinal vessel, the computer program product comprising a computer-readable storage medium having computer-readable program code means embodied in said medium, said computer-readable program code means comprising:

first computer-readable program code means for determining a relationship between an error in a blood oxygen saturation measurement and measurement errors in the respective transmittances of the blood within the retinal vessel for light at a plurality of wavelengths;

second computer-readable program code means, responsive to said first computer-readable program code means, for determining, for each of a plurality of different combinations of wavelengths, the error in the blood oxygen saturation measurement for retinal vessels having a range of vessel diameters and a range of blood oxygen saturation values; and third computer-readable program code means, responsive to said second computer-readable program code means, for displaying, for each of a plurality of different combinations of wavelengths, the error in the blood oxygen saturation measurement for retinal vessels having a range of vessel diameters and a range of blood oxygen saturation values to thereby facilitate selection of a combination of wavelengths of light.

14. A computer program product according to claim 13 wherein said first computer-readable program code means comprises computer-readable program code means for determining a relationship between the blood oxygen saturation of the retinal vessel and the respective transmittances of the blood within the retinal vessel for light at the plurality of wavelengths.

15. A computer program product according to claim 13 wherein said first computer-readable program code means comprises fourth computer-readable program code means for determining the error $\Delta s$ in the blood oxygen saturation measurement as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)}$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

16. A computer program product according to claim 15 wherein said fourth computer-readable program code means further comprises computer-readable program code means for determining, for each of the plurality of different combinations of wavelengths, the error in the blood oxygen saturation measurement arising from respective measurement errors $\Delta T^{\lambda_n}$ in the transmittance of the blood within the retinal vessel for light at each of the different wavelengths.

17. An apparatus for measuring blood oxygen saturation within a retinal vessel based upon a transmittance of the blood within the retinal vessel, the apparatus comprising:

means for selecting a combination of wavelengths of light based upon a corresponding error in a blood oxygen saturation measurement, said selecting means comprising:

means for determining a relationship between the error in the blood oxygen saturation measurement and measurement errors in the respective transmittances of the blood within the retinal vessel for light at a plurality of wavelengths; and means for determining, for each of a plurality of different combinations of wavelengths, the error in the blood oxygen saturation measurement for retinal vessels having a range of vessel diameters and a range of blood oxygen saturation values;

an optical source for illuminating the retinal vessel with light having the selected combination of wavelengths;

a detector for measuring the transmittance of the blood within the retinal vessel in response to illumination at each of the selected wavelengths; and means, responsive to said detector, for determining the blood oxygen saturation within the retinal vessel based upon the respective transmittances of the blood within the retinal vessel measured by said detector at each of the selected wavelengths.

18. An apparatus according to claim 17 wherein said means for determining a relationship comprises means for determining a relationship between the blood oxygen saturation of the retinal vessel and the respective transmittances of the blood within the retinal vessel for light at the plurality of wavelengths.

19. An apparatus according to claim 17 wherein said means for determining a relationship comprises means for determining the error $\Delta s$ in the blood oxygen saturation measurement as follows:

$$\Delta s = \sqrt{\left(\frac{\partial s}{\partial T^{\lambda_1}} \cdot \Delta T^{\lambda_1}\right) + \ldots + \left(\frac{\partial s}{\partial T^{\lambda_n}} \cdot \Delta T^{\lambda_n}\right)}$$

wherein n is an integer designating respective ones of the plurality of wavelengths, wherein $T^{\lambda_n}$ represents the transmittance of the blood within the retinal vessel for light at the $n^{th}$ wavelength, wherein $\Delta T^{\lambda_n}$ represents the measurement error in the transmittance of the blood within the retinal vessel for light at the $n^{th}$ wavelength, and wherein $$\frac{\partial s}{\partial T}$$

is a partial derivative of the calculated blood oxygen saturation s with respect to the transmittance of blood within the retinal vessel.

20. An apparatus according to claim 19 wherein said means for determining the error in the blood oxygen saturation measurement comprises means for determining, for each of the plurality of different combinations of wavelengths, the error in the blood oxygen saturation measurement arising from respective measurement errors $\Delta T^{\lambda_n}$ in the transmittance of the blood within the retinal vessel for light at each of the different wavelengths which are each less than a predetermined transmittance error.

21. An apparatus for measuring blood oxygen saturation within a retinal vessel based upon a transmittance of the blood within the retinal vessel, the apparatus comprising:

a first optical source for illuminating the eye with light having a first wavelength between 460 nm and 503 nm;

a second optical source for illuminating the eye with light having a second wavelength between 600 nm and 770 nm;

a third optical source for illuminating the eye with light having a third wavelength between 770 nm and 1100 nm;

a detector for measuring the transmittance of the blood within the retinal vessel in response to illumination by each of said first, second and third optical sources; and means, responsive to said detector, for determining the blood oxygen saturation within the retinal vessel based upon the respective transmittances of the blood within the retinal vessel measured by said detector at each of the first, second and third wavelengths.

* * * * *